United States Patent
Handa et al.

(12)

(10) Patent No.: US 6,384,213 B1
(45) Date of Patent: May 7, 2002

(54) PROCESS FOR PREPARING A PURE, PHARMACOPOEIAL GRADE AMORPHOUS FORM OF CEFUROXIME AXETIL

(75) Inventors: Vijay Kumar Handa, Hyderabad; Om Dutt Tyagi; Uttam Kumar Ray, both of New Delhi, all of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/574,311

(22) Filed: May 19, 2000

Related U.S. Application Data (63) Continuation-in-part of application No. 09/300,976, filed on Apr. 28, 1999, now abandoned, which is a continuation-in-part of application No. 09/178,157, filed on Oct. 23, 1998, now abandoned.

(51) Int. Cl.$^7$ .............................................. C07D 501/34
(52) U.S. Cl. ...................................................... 540/222
(58) Field of Search ......................................... 540/222

(56) References Cited

U.S. PATENT DOCUMENTS

| 4,267,320 A | 5/1981 | Gregson et al. | 544/22 |
| 4,562,181 A | 12/1985 | Crisp et al. | 540/222 |
| 4,775,750 A | 10/1988 | White et al. | 540/222 |
| 4,820,833 A | 4/1989 | Crisp et al. | 540/222 |
| 4,994,567 A | 2/1991 | Crisp et al. | 540/222 |
| 5,013,833 A | 5/1991 | Crisp et al. | 540/222 |
| 5,847,118 A | 12/1998 | Karimian et al. | 540/222 |

FOREIGN PATENT DOCUMENTS

| EP | 0 757 991 A1 | 2/1997 |
| WO | WO 98/43980 | 10/1998 |

*Primary Examiner*—Mark L Berch
(74) *Attorney, Agent, or Firm*—Jayadeep R. Deshmukh, Esq.

(57) ABSTRACT

There is described a process for the preparation of a pure amorphous form of cefuroxime axetil which involves dissolving crystalline cefuroxime axetil in acetic acid including at least 5% v/v water and recovering said amorphous form of cefuroxime axetil from the solution by the addition of additional water, the solution being added all at once to the additional water being present in a volume which is sufficient to precipitate said amorphous cefuroxime axetil.

3 Claims, 10 Drawing Sheets

FIG. 7
IR spectrum (KBr) of Amorphous Cefuroxime axetil

PROCESS FOR PREPARING A PURE, PHARMACOPOEIAL GRADE AMORPHOUS FORM OF CEFUROXIME AXETIL

RELATED APPLICATIONS

This application is a continuation-in-part of U.S. patent application Ser. No. 09/300,976 filed Apr. 28, 1999, abandoned which is a continuation-in-part of U.S. patent application Ser. No. 09/178,157 filed Oct. 23, 1998 abandoned.

FIELD OF THE INVENTION

The present invention relates to a process for the preparation of a pure pharmacopoeial grade amorphous form of cefuroxime axetil.

BACKGROUND OF THE INVENTION

Cefuroxime axetil is 1-acetoxyethyl ester of cefuroxime, a second generation cephalosporin antibiotic with a broad spectrum of activity against gram-positive and gram-negative microorganisms. This compound, as well as many other esters of cefuroxime, are disclosed and claimed in U.S. Pat. No. 4,267,320. This patent discloses conventional methods for preparing a mixture of the R and S isomers in crystalline form, as well as for separating the individual R and S diastereoisomers.

U.S. Pat. No. 4,562,181 and related U.S. Pat. Nos. 4,820,833, 4,994,567 and 5,013,833 all disclose that cefuroxime axetil in amorphous form essentially free from crystalline material and having a purity of at least 95% (not including residual solvents), has a higher bioavailability than the crystalline form while also having adequate chemical stability. These patents disclose that highly pure cefuroxime axetil can be recovered in substantially amorphous form from a solution containing cefuroxime axetil by spray drying, roller drying, or solvent precipitation. The preferred method is spray drying. In each case, crystalline cefuroxime axetil is dissolved in an organic solvent and the cefuroxime axetil is recovered from the solution in a highly pure, substantially amorphous form by one of the foregoing methods. The prior art processes for the preparation of amorphous form of cefuroxime axetil suffer from disadvantages and also are not convenient to operate at a large scale. These disadvantages include requiring large volume of solvents for dissolving cefuroxime axetil because of the poor solubility of cefuroxime axetil in the solvents utilized by the prior art. This is uneconomical on a commercial scale because large size reactors would be necessary. Furthermore, because of the poor solubility, cefuroxime axetil needs to be dissolved at higher temperature followed by concentration of the solution to reduce the volume. These disadvantages make the processes of the prior art operationally tedious and inefficient.

U.S. Pat. No. 5,847,118 ("the '118 patent") discloses a method of preparing amorphous cefuroxime axetil which comprises dissolving crystalline cefuroxime axetil in a solvent such as formic acid, the solvent being present in an amount just sufficient to dissolve the crystalline cefuroxime axetil, and later adding the resulting cefuroxime axetil solution to water. All the examples of the patent only disclose dropwise addition of the cefuroxime axetil solution to water. As is shown by the present invention, certain advantages are realized if the cefuroxime axetil solution is added all at once (dumped) into the water instead of the dropwise addition disclosed by the '118 patent. Thus, it is observed that the crystallinity of the resulting product is greatly reduced, i.e., the product is much more completely amorphous by use of the dumping method of the present invention. Additionally, it has been determined that a specific volume of water is required in relationship to the weight of the crystalline cefuroxime axetil (starting material) for precipitation of an amorphous product that contains as little crystalline material as possible. Thus, it is believed that a sufficient amount of water is required, into which the cefuroxime axetil solution is added all at once. It is preferred that at least 25 times the volume of water in comparison to the weight of crystalline cefuroxime axetil be used.

SUMMARY OF THE INVENTION

It is an object of the present invention to obtain a pure, pharmacopoeial grade amorphous form of cefuroxime axetil by a process which is efficient and commercially viable. Cefuroxime Axetil in accordance with the invention has a purity by chromatographic analysis (chemical purity) of at least 95% w/w, preferably containing less than 3% w/w and is in pharmacopoeial grade amorphous form (meeting the specifications as per U.S. Pharmacopoeia 23).

Accordingly, the present invention provides a process for the preparation of a pure, pharmacopoeial grade amorphous form of cefuroxime axetil which comprises dissolving crystalline cefuroxime axetil in acetic acid including at least about 5% v/v water and recovering said amorphous form of cefuroxime axetil from said solution by the addition of water, the solution being dumped into the water and the water being present in a volume which is sufficient to precipitate the amorphous cefuroxime axetil. It is preferred that the volume of water into which the solution is dumped is at least 25 times the weight of the crystalline cefuroxime axetil.

In accordance with the present invention, cefuroxime axetil in crystalline form (the starting material) is dissolved in acetic acid containing at least about 5% v/v water at a temperature of at least about 50° C. After it is completely dissolved, the solution is added to precooled water (0–20° C.) under vigorous stirring, the water being present in a volume which is preferably at least 25 times the weight of the crystalline cefuroxime axetil. At least 30 times the volume of water is more preferred and at least 40 times is even more preferred. Precipitated cefuroxime axetil is filtered, washed with water and dried under vacuum.

Preferably, the volume of solvent is at least about 1.6 parts per part of the starting material. Higher volumes of solvents and generally up to 10 parts per part of the starting material can be used. Volumes higher than 10 parts are not useful from an economical point of view. The volume of solvent in relation to the amount of starting material can be adjusted based on the temperature and Is known to a person of ordinary skill in the art.

Generally, the product can be collected by any standard method known in the art such as by filtration, filtration under vacuum or decantation and drying.

BRIEF DESCRIPTION OF THE INVENTION

The present invention is further illustrated by the following examples, none of which should be construed as limiting the scope of this invention in any way:

Comparative Example 1

Figure 1:
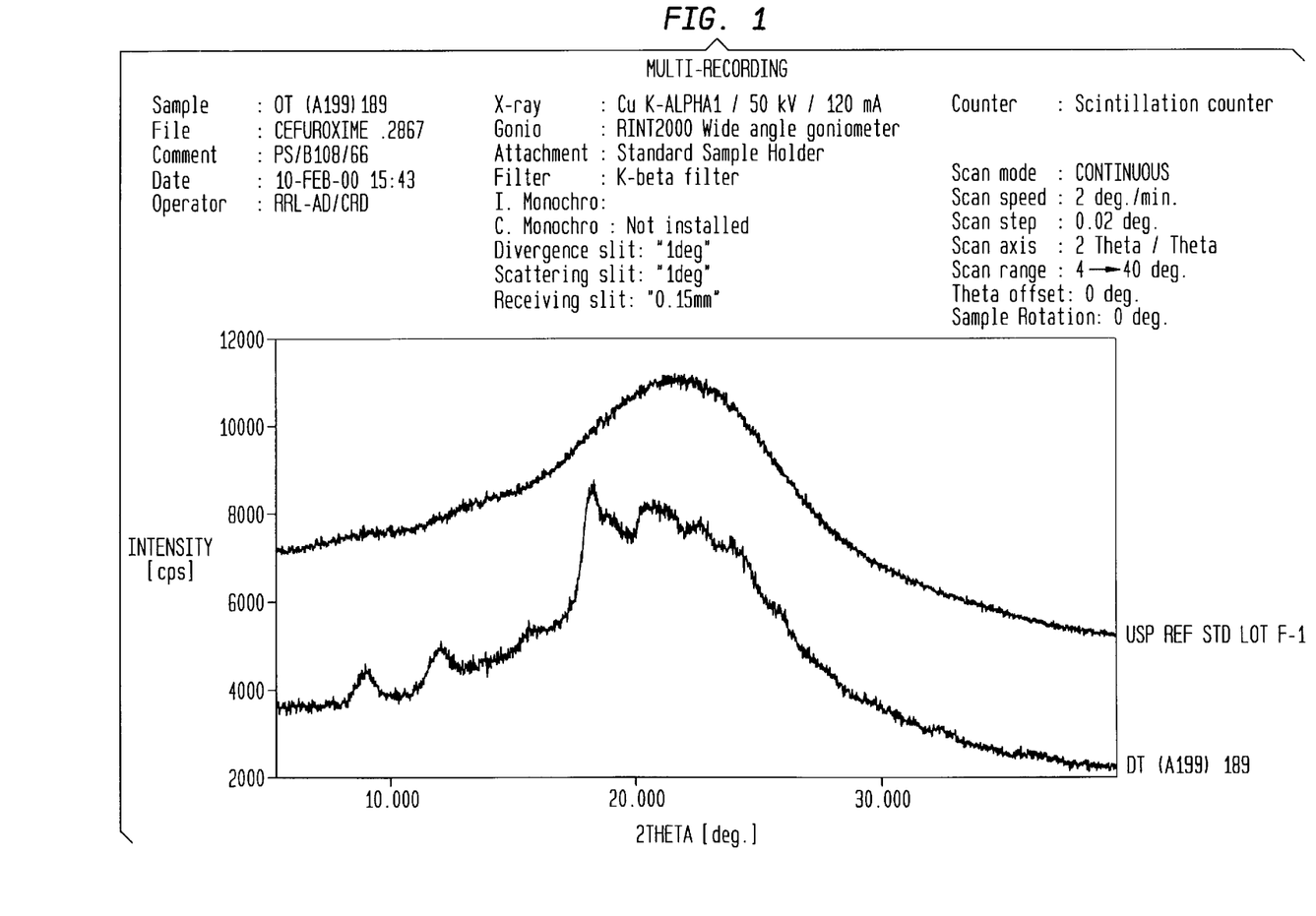
FIG. 1 shows the X-ray powder diffraction patterns of the batch made according to Comparative Example 1, in comparison with United States Pharmacopoeial (USP) reference standard.

Example 5 of the '118 patent was followed. Thus, cefuroxime axetil (100 g) was dissolved in 152 ml 88% cold formic acid. The resulting solution was added dropwise to ice cold deionized water (2000 ml) with good mechanical stirring. A thick slurry formed which was filtered and washed with a small quantity of ice cold deionized water. The damp cake was pulped in ice cold deionized water (400 ml) for 10 minute, filtered and washed. Pulping was repeated once more. The cake was then dried under a stream of nitrogen for 72 hours and then dried under vacuum at 40–45° C. for 48 hours. FIG. 1 shows the X-ray diffraction patterns of this batch in comparison with United States Pharmacopoeial (USP) reference standard. In comparison to the white to almost white amorphous powder per USP, the powder per this method was off white. Per infra red spectroscopy, the powder by this method does not comply with the USP reference standard. The powder according to this method has 20% crystallinity which does not comply with the USP reference standard. USP requires that the anti isomers A and B be not more than 1%, whereas the powder per this method has 1.20% anti isomers A and B.

Comparative Example 2

Figure 2:
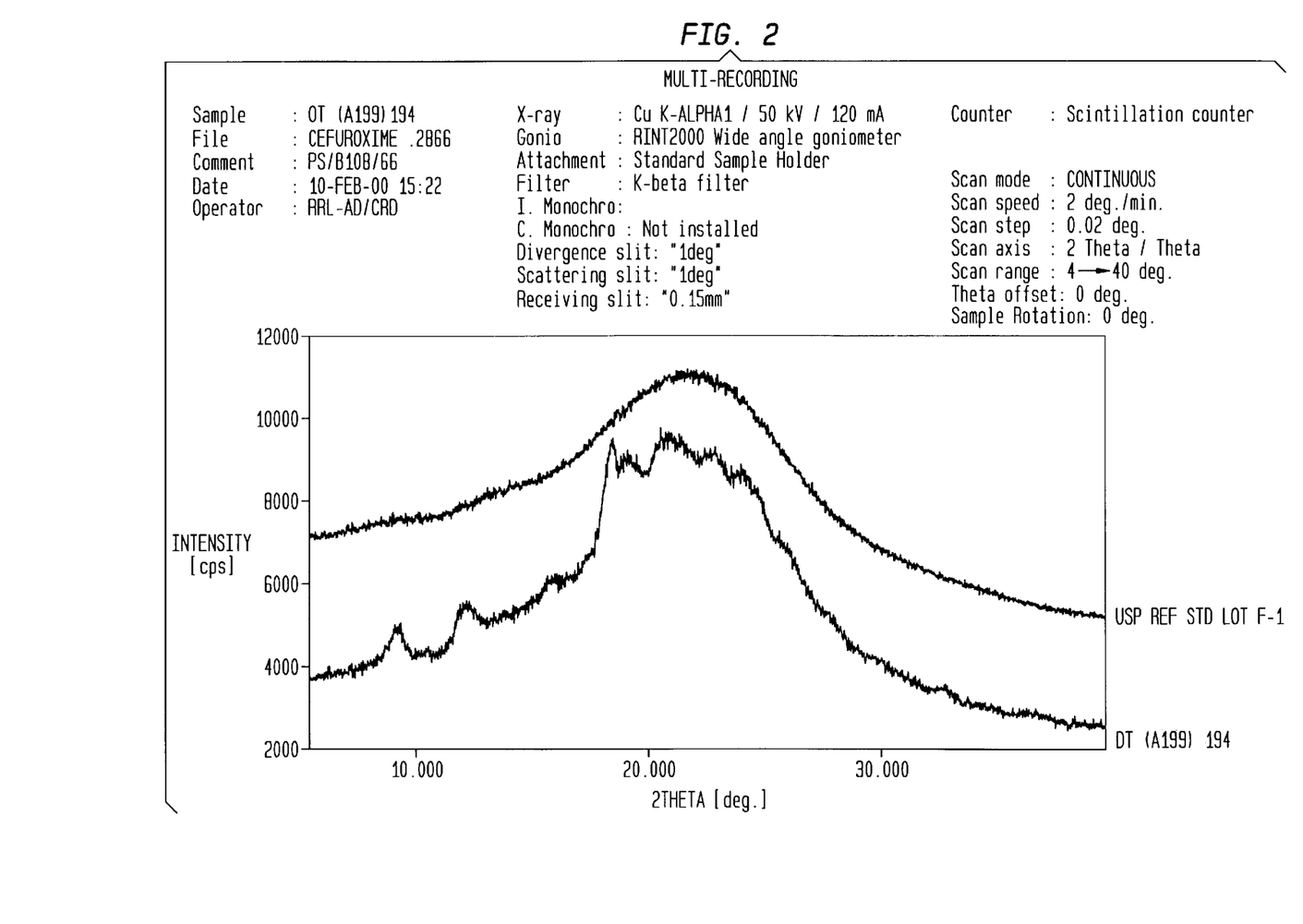
FIG. 2 shows the X-ray powder diffraction patterns of the batch made according to Comparative Example 2, in comparison with United States Pharmacopoeial (USP) reference standard.

Example 6 of the '118 patent was followed. Thus, cefuroxime axetil (100 g) was dissolved in 105 ml 96% cold formic acid. The resulting solution was added dropwise to ice cold deionized water (2000 ml) with good mechanical stirring. A thick slurry formed which was filtered and washed with a small quantity of ice cold deionized water. The damp cake was pulped in ice cold deionized water (400 ml) for 10 minute, filtered and washed. Pulping was repeated once more. The cake was then dried under a stream of nitrogen for 72 hours and then dried under vacuum at 40–45° C. for 48 hours. FIG. 2 shows the X-ray powder diffraction patterns of this batch in comparison with United States Pharmacopoeial (USP) reference standard. In comparison to the white to almost white amorphous powder per USP (USP 23), the powder per this method was pale yellow. Per infrared spectroscopy, the powder by this method does not comply with the USP reference standard. The powder according to this method has 20% crystallinity which does not comply with the USP reference standard. USP requires that the anti isomers A and B be not more than 1%, whereas the powder per this method has 2.00% anti isomers A and B.

Comparative Example 3

Figure 3:
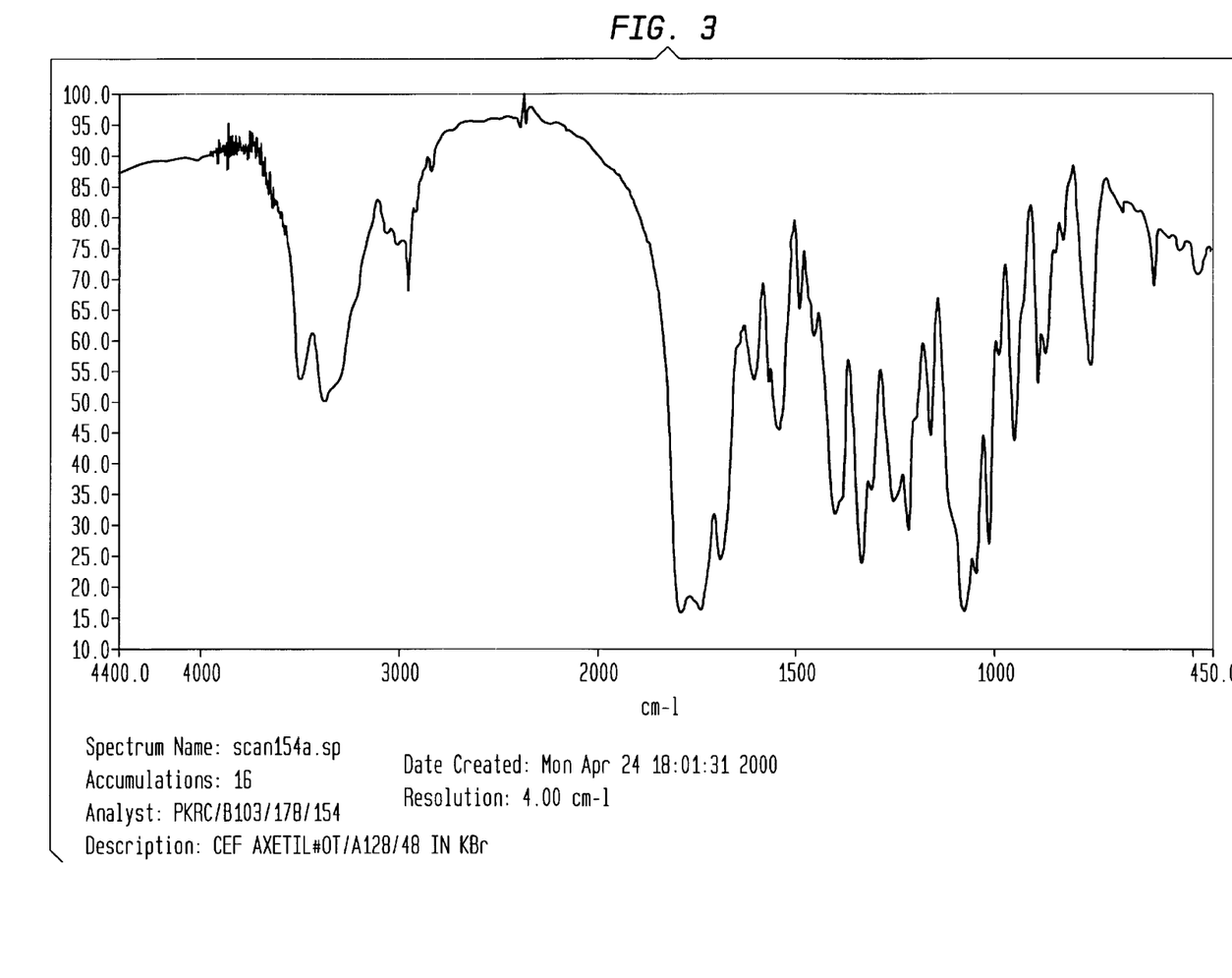
FIG. 3 is the infrared spectrum of the cefuroxime axetil made in accordance with Comparative Example 3.
Figure 4:
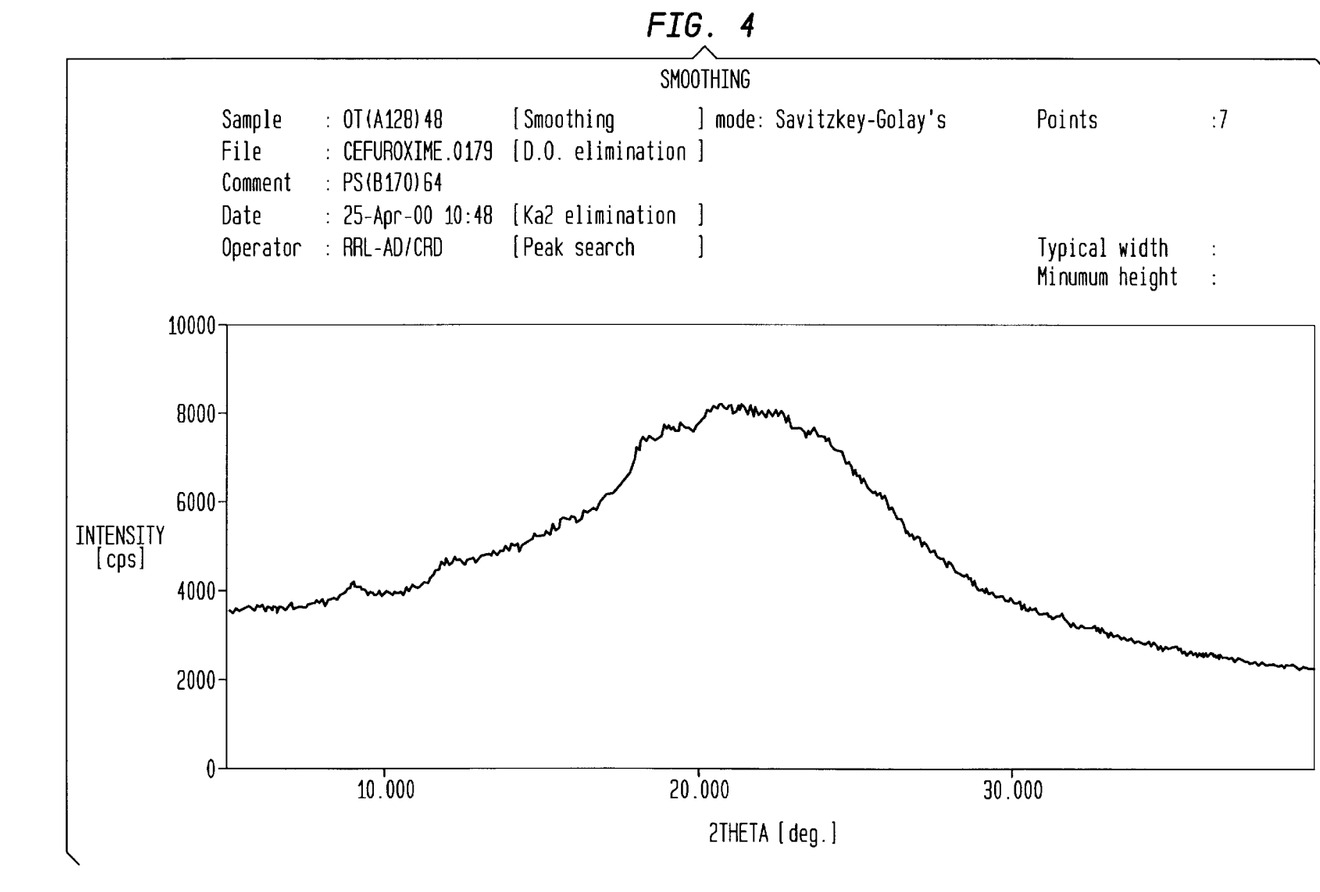
FIG. 4 shows X-ray powder diffraction (XRD) pattern of the cefuroxime axetil made in accordance with Comparative Example 3.

Example 5 of the '118 patent (Comparative Example 1 above) was followed, with the exception that the solution was added all at once to the water (as opposed to dropwise). This resulted in a powder having about 12% crystallinity. The IR and X-Ray diffraction pattern of this powder is shown in FIGS. 3 and 4.

Comparative Example 4

Figure 5:
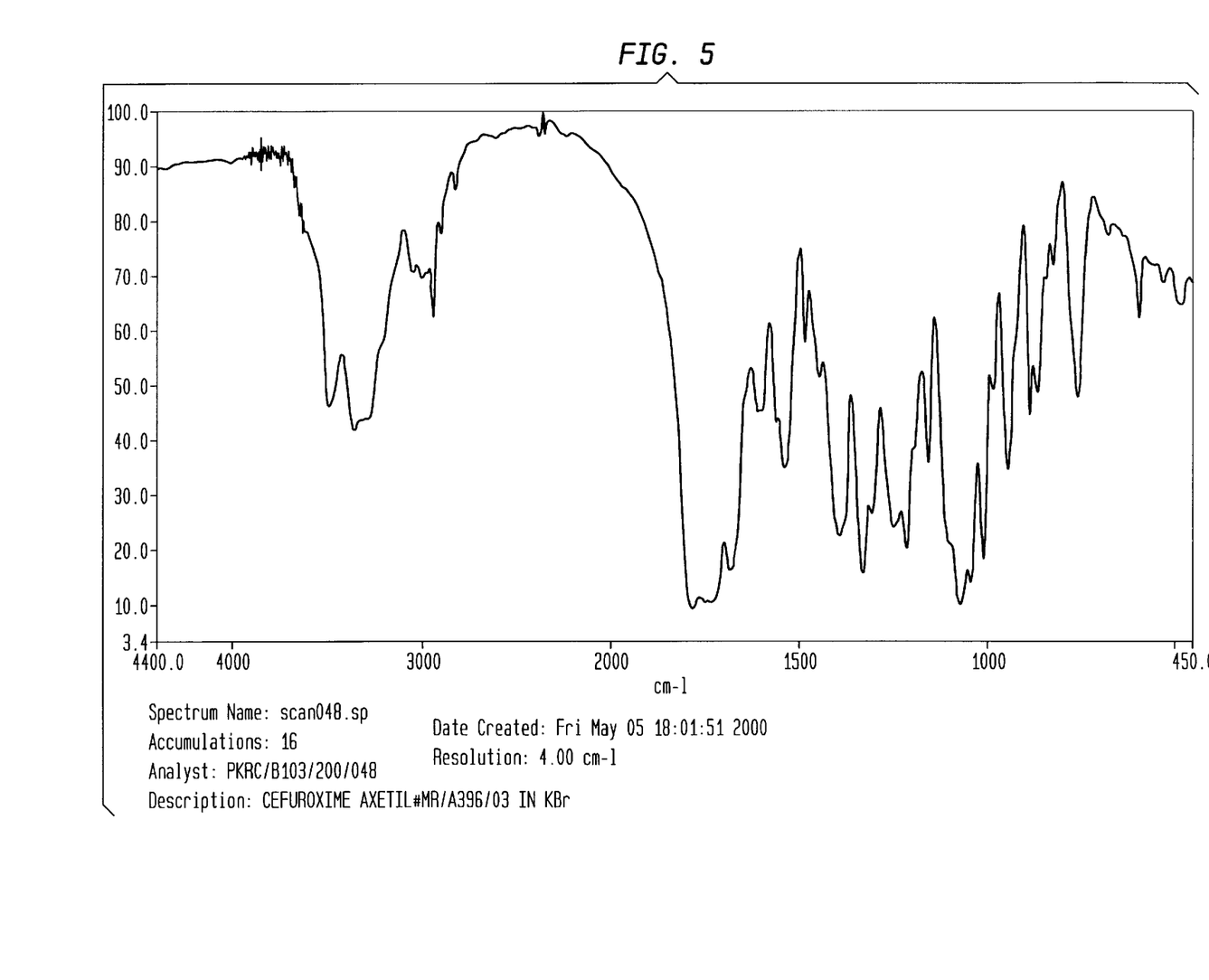
FIG. 5 is the infrared spectrum of the cefuroxime axetil made in accordance with Comparative Example 4.
Figure 6:
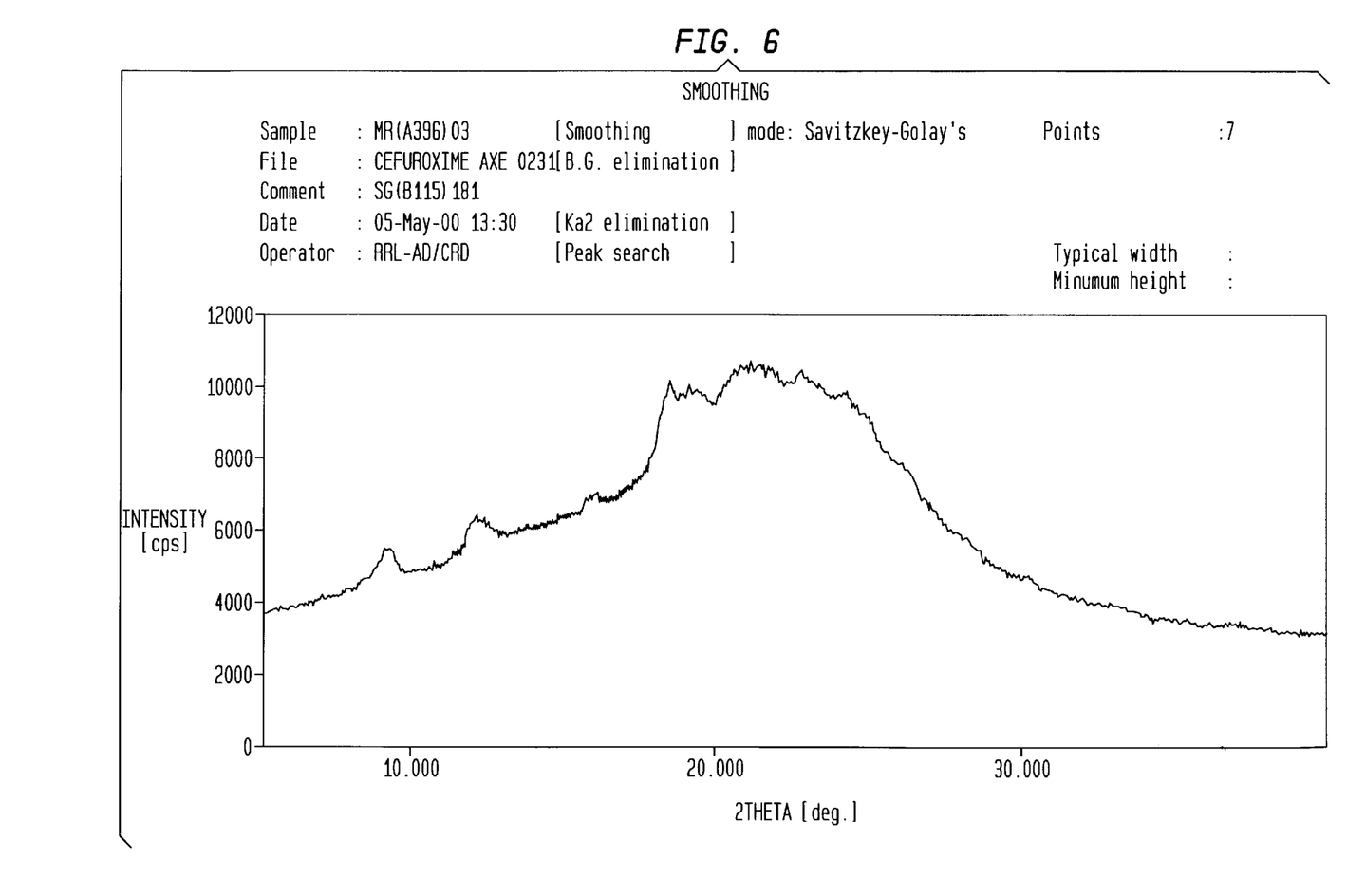
FIG. 6 shows X-ray powder diffraction (XRD) pattern of the cefuroxime axetil made in accordance with Comparative Example 4.

Example 5 of the '118 patent (Comparative Example 1 above) was followed, with the exception that the cefuroxime axetil was dissolved in acetic acid (88%, 152 ml) at 85° C. (as it did not dissolve in cold acetic acid). This resulted in a powder having about 18% crystallinity. The IR and X-Ray diffraction pattern of this powder is shown in FIGS. 5 and 6.

EXAMPLE 1

Figure 7:
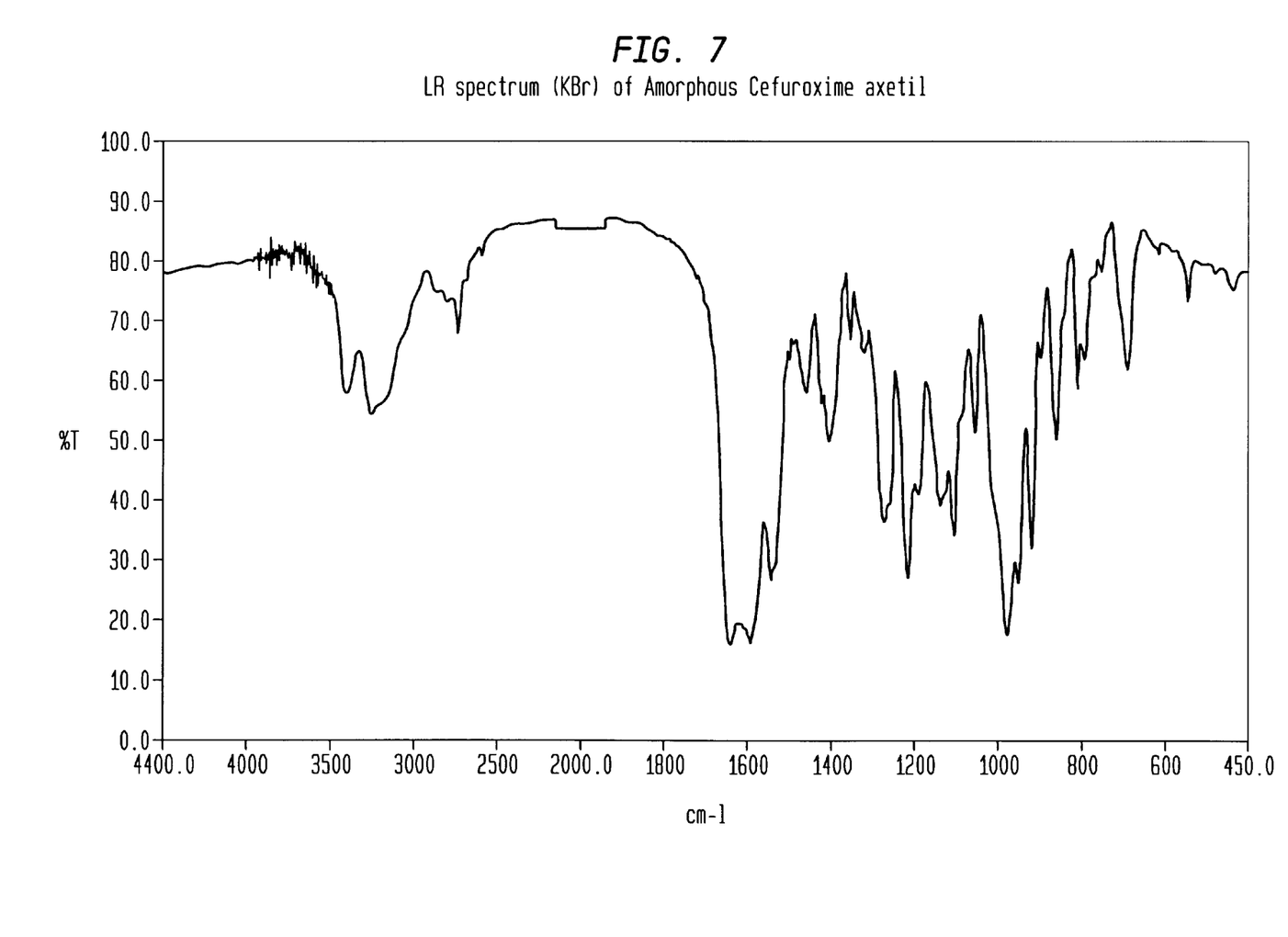
FIG. 7 is the infrared spectrum of the amorphous cefuroxime axetil made in accordance with Example 1.
Figure 8:
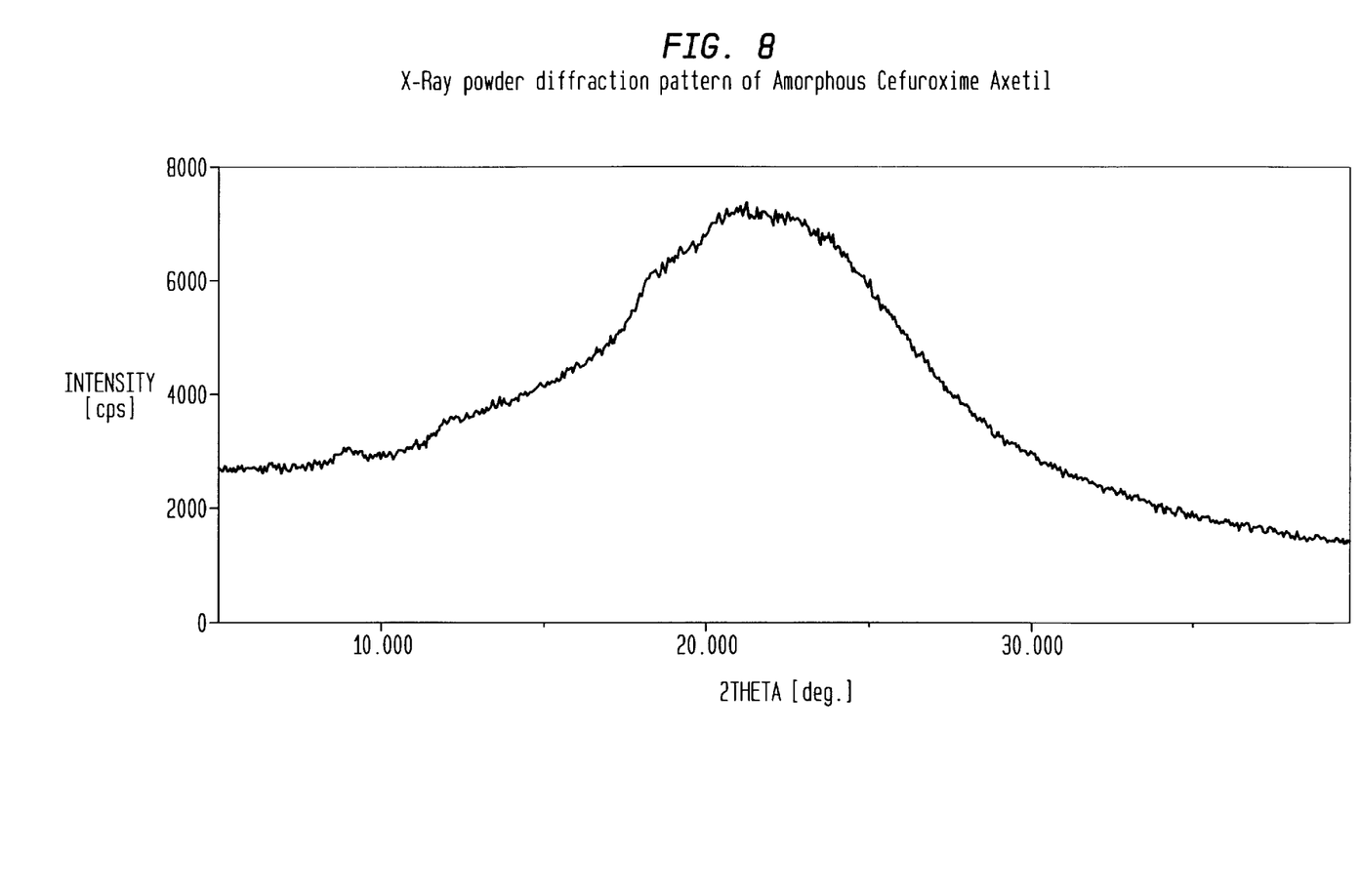
FIG. 8 shows X-ray powder diffraction (XRD) pattern of the amorphous cefuroxime axetil made in accordance with Example 1.

Crystalline cefuroxime axetil (a mixture of R and S isomers, ca 1:1) (50 g) was dissolved in acetic acid (100 ml) and water (12 ml) at 65–70° C. The resulting clear solution was added all at once (dumped into) to vigorously stirred cold water (3000 ml). The product thus precipitated was filtered and washed with cold water (1000 ml). The wet cake was dried in Fluid Bed Dryer at 45–60° C. for 3.0 hr and then dried under vacuum at 40–45° C. to give 42.0 g amorphous form of cefuroxime axetil. IR (KBr) spectrum (FIG. 7) and X-ray powder diffraction pattern (FIG. 8) confirmed that the product was amorphous. The product was analyzed by HPLC and was found to be 99.11% w/w with diastereoisomeric ratio 0.53 and impurities level 0.53% w/w. Acetic acid content in the finished product was 0.11% w/w on analysis by capillary electrophoresis. It is believed that the surprisingly high purity level is due to the use of acetic acid by itself and without formic acid. The use of the weaker acetic acid (as compared to formic acid) is believed also to reduce the degradation of cefuroxime axetil. Additionally, acetic acid is a cheap, commercially available solvent and can be handled safely without any special effort. As compared to acetic acid, other solvents such as dimethyl formamide, dimethylacetamide and dimethylsulfoxide remain as residual solvent in amorphous cefuroxime axetil at a much higher level than the prescribed limits and also it results in lower potency of the product.

EXAMPLE 2

Crystalline cefuroxime axetil (a mixture of R and S isomers, ca 1:1) (25 g) was dissolved in acetic acid (50 ml) and water (6 ml) at about 70° C. The resulting clear solution was added in one lot to ice cold water (625 ml) with vigorous stirring. The product thus precipitated was filtered and washed with water (1500 ml) and dried as described above. It was confirmed by IR spectrum and X-ray diffraction pattern that the product was amorphous.

EXAMPLE 3

Figure 9:
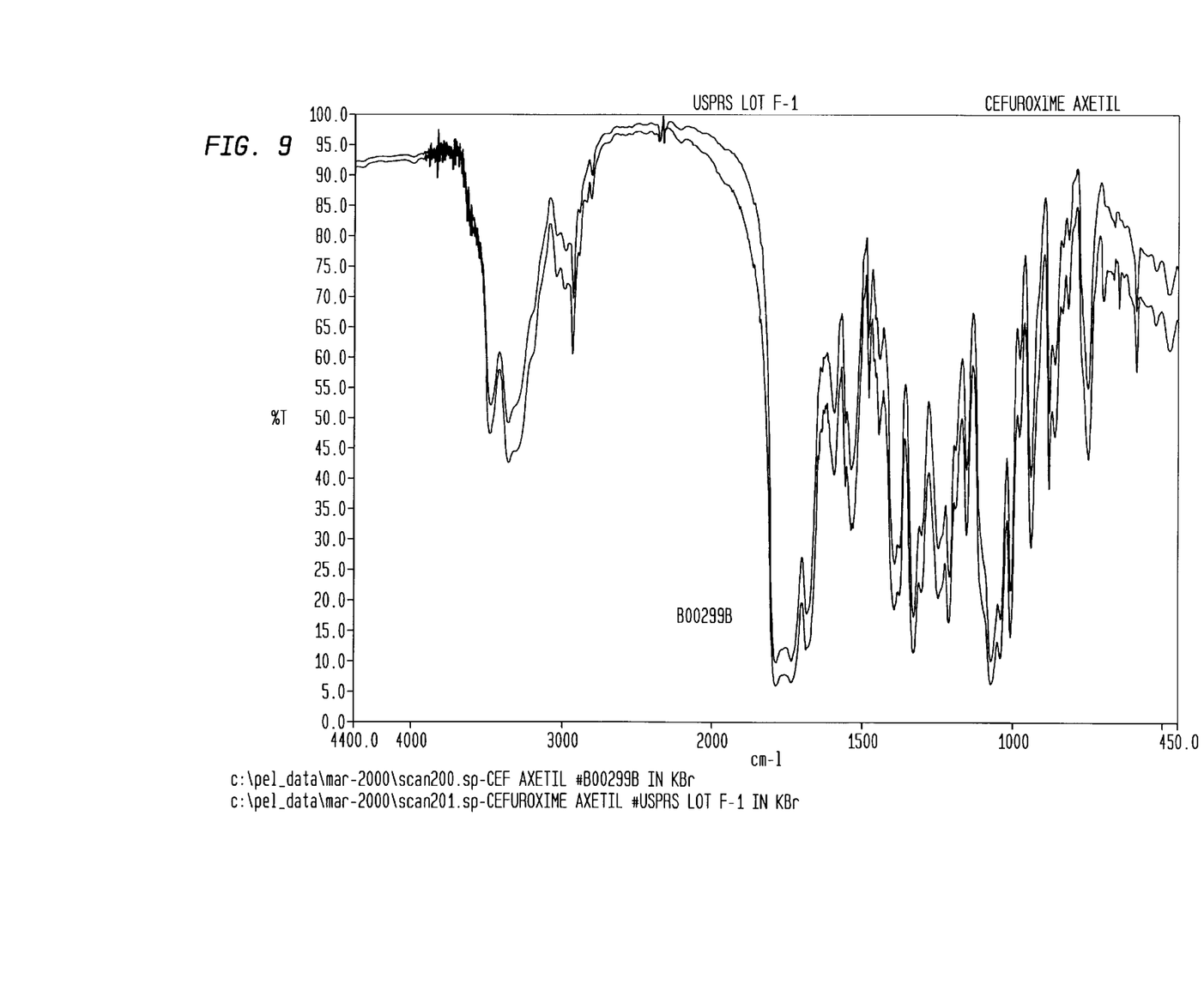
FIG. 9 is the infrared spectrum of the amorphous cefuroxime axetil made in accordance with Example 3, in comparison with United States Pharmacopoeial (USP) reference standard.
Figure 10:
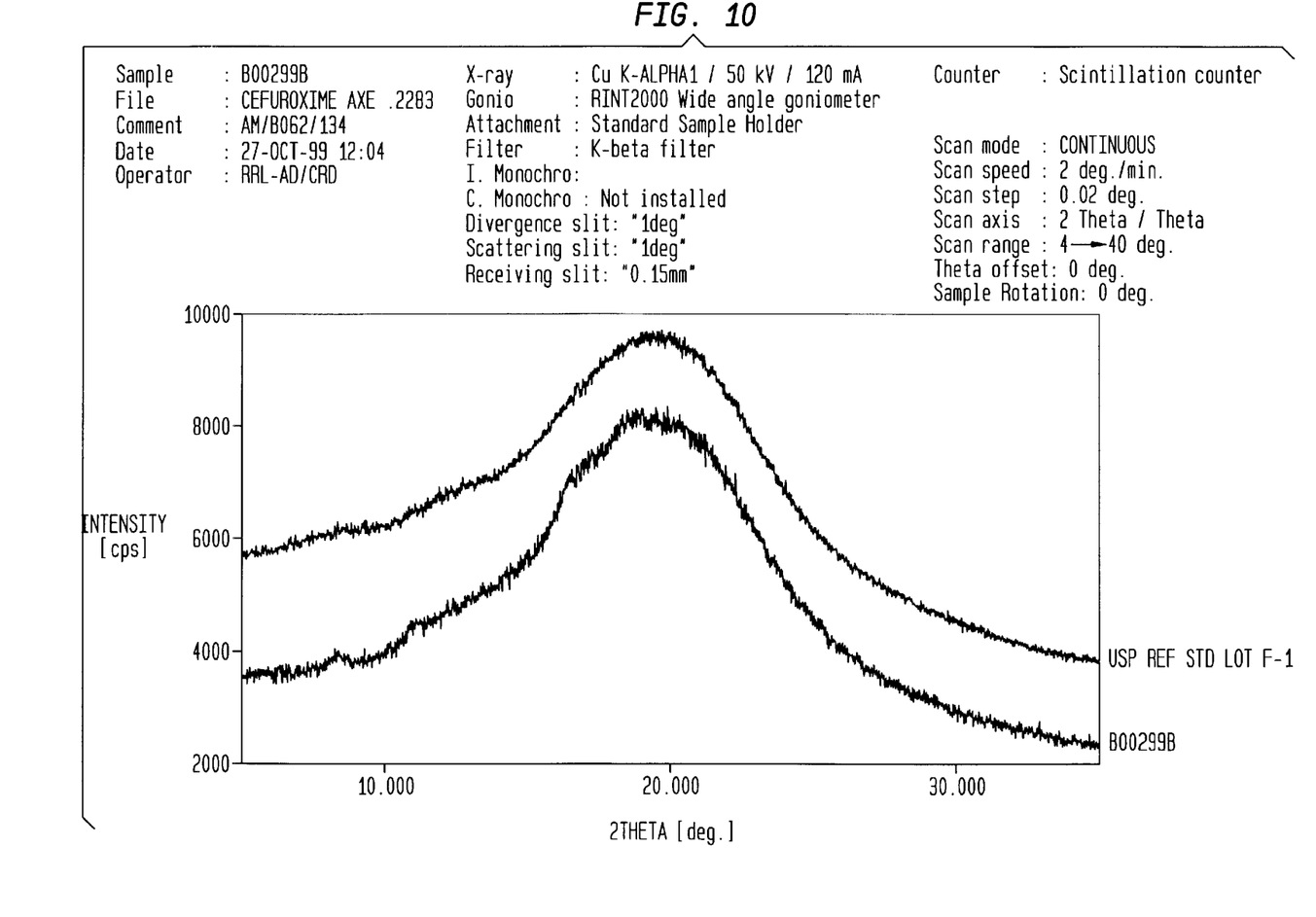
FIG. 10 shows X-ray powder diffraction (XRD) pattern of the amorphous cefuroxime axetil made in accordance with Example 3, in comparison with United States Pharmacopoeial (USP) reference standard.

A mixture of R and S isomers (ca 1:1) of crystalline cefuroxime (10.0 kg) was added to a preheated (55–65°C.)

mixture of glacial acetic acid (20.0 lt) and deionized water (2.4 lt) and stirred at 65–70° C. till a clear solution was obtained. The resulting clear solution was dumped in one lot to a precooled deionized water (400 lt, 0–1° C.) under vigorous stirring and the stirring was continued further for 2–3 minutes. The solid thus precipitated was centrifuged quickly, washed the wet cake with cold deionized water (600 lt, 0–3° C.) and continued spinning for 60 minutes. The wet product was dried in a Fluid Bed Dryer (FBD) with air at 20–45° C. till the water content was less than 2.5% w/w. The drying took ~6 hrs. during which the product was suitably milled and passed through sieve to avoid the lump formation and case hardening. The free flowing powder thus obtained was finally dried under reduced pressure at 35–40° C. till the water content was not more than 1.2% w/w (for ~4 hours) to give 8.3 Kg of pure amorphous cefuroxime axetil. IR (KBr) spectrum (FIG. 9) and X-ray powder diffraction pattern (FIG. 10) confirmed that the product was amorphous.

We claim:

1. A process for the preparation of a pure amorphous form of cefuroxime axetil which comprises dissolving crystalline cefuroxime axetil in acetic acid including at least 5% v/v water and recovering said amorphous form of cefuroxime axetil from the solution by the addition of additional water, the solution being added all at once to the additional water and the additional water being present in a volume which is sufficient to precipitate said amorphous cefuroxime axetil.

2. The process of claim 1, where in said crystalline cefuroxime axetil is dissolved in acetic acid at a temperature of at least about 50° C.

3. The process of claim 2 wherein said crystalline cefuroxime axetil is dissolved in acetic acid at a temperature of at least about 60° C.

* * * * *